(12) United States Patent
Jung et al.

(10) Patent No.: US 11,622,651 B2
(45) Date of Patent: Apr. 11, 2023

(54) AUTOMATIC COOKING DEVICE AND METHOD

(71) Applicant: SAMSUNG ELECTRONICS CO., LTD., Suwon-si (KR)

(72) Inventors: Hyun-ki Jung, Seoul (KR); Jun-beom Han, Seoul (KR); Sang-min Lee, Hwaseong-si (KR); Byeong-hoon Kwak, Uiwang-si (KR); Joon-hyun Lee, Seoul (KR); Sung-hoon Yim, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 16/643,397

(22) PCT Filed: Jul. 11, 2018

(86) PCT No.: PCT/KR2018/007839
§ 371 (c)(1),
(2) Date: Feb. 28, 2020

(87) PCT Pub. No.: WO2019/066216
PCT Pub. Date: Apr. 4, 2019

(65) Prior Publication Data
US 2021/0068582 A1 Mar. 11, 2021

(30) Foreign Application Priority Data
Sep. 29, 2017 (KR) .................. 10-2017-0128302

(51) Int. Cl.
*A47J 36/32* (2006.01)
*A47J 37/06* (2006.01)
(Continued)

(52) U.S. Cl.
CPC ......... *A47J 36/321* (2018.08); *A47J 37/0629* (2013.01); *A47J 37/0664* (2013.01);
(Continued)

(58) Field of Classification Search
CPC .. A47J 36/321; A47J 37/0664; A47J 37/0629; G01N 21/31; G01N 33/02
(Continued)

(56) References Cited

U.S. PATENT DOCUMENTS 4,633,065 A * 12/1986 Takazume ............ H05B 6/6452
                                                          219/396
5,729,703 A    3/1998 Onn et al.
(Continued)

FOREIGN PATENT DOCUMENTS

CN   101692958 A  *  4/2010  ............ A47J 27/004
CN   203810478 U     9/2014
(Continued)

OTHER PUBLICATIONS

Communication dated Jun. 2, 2021, issued by the Intellectual Property Office of India in Indian Application No. 202017007662.
(Continued)

*Primary Examiner* — Thien S Tran
(74) *Attorney, Agent, or Firm* — Sughrue Mion, PLLC

(57) ABSTRACT

The present disclosure relates to an artificial intelligence (AI) system for simulating functions, such as recognition and determination, of the human brain by using a machine learning algorithm such as deep learning, and an application thereof. Provided are an automatic cooking device and method for selectively emitting light of different wavelength bands to a food material, identifying the food material by obtaining information about the food material, based on reflected light, and controlling a cooking process of the food material.

11 Claims, 8 Drawing Sheets

(51) Int. Cl.
  *G01N 21/31* (2006.01)
  *G01N 33/02* (2006.01)
  *G06N 3/08* (2006.01)
  *G06N 3/02* (2006.01)
  *G01N 21/17* (2006.01)
  *F24C 7/08* (2006.01)
  *F24C 5/16* (2006.01)
  *F24C 3/12* (2006.01)
  *G06V 20/00* (2022.01)

(52) U.S. Cl.
  CPC ............... *F24C 3/128* (2013.01); *F24C 5/16* (2013.01); *F24C 7/085* (2013.01); *G01N 21/17* (2013.01); *G01N 21/31* (2013.01); *G01N 33/02* (2013.01); *G06N 3/02* (2013.01); *G06N 3/08* (2013.01); *G06V 20/00* (2022.01); *G03B 2219/00* (2013.01); *G05B 2219/2651* (2013.01)

(58) Field of Classification Search
  USPC .................. 219/412, 413; 426/127, 231
  See application file for complete search history.

(56) References Cited

U.S. PATENT DOCUMENTS

| | | | |
|---|---|---|---|
| 9,069,340 B2 | 6/2015 | Minvielle | |
| 9,562,848 B2 | 2/2017 | Goldring et al. | |
| 9,839,318 B2 | 12/2017 | Lagerlof | |
| 10,572,732 B2 | 2/2020 | Park et al. | |
| 2012/0237644 A1* | 9/2012 | Luckhardt | G01N 33/12 324/693 |
| 2014/0044841 A1* | 2/2014 | Luckhardt | A23L 5/10 324/693 |
| 2015/0064314 A1* | 3/2015 | Manuel | A47J 36/321 707/731 |
| 2016/0150213 A1 | 5/2016 | Mutti et al. | |
| 2016/0213189 A1 | 7/2016 | Yoon et al. | |
| 2016/0327281 A1 | 11/2016 | Bhogal et al. | |
| 2016/0348918 A1 | 12/2016 | Bhogal et al. | |
| 2017/0115008 A1 | 4/2017 | Erbe et al. | |
| 2017/0167733 A1* | 6/2017 | Bockler | G01K 13/00 |

FOREIGN PATENT DOCUMENTS

| | | | |
|---|---|---|---|
| CN | 105708306 A | * | 2/2016 |
| CN | 105444222 A | | 3/2016 |
| CN | 105708306 A | | 6/2016 |
| CN | 105851782 A | * | 8/2016 |
| CN | 106535384 A | | 3/2017 |
| CN | 106871570 A | | 6/2017 |
| CN | 108140328 A | | 6/2018 |
| DE | 102005014713 A1 | | 10/2006 |
| DE | 102012204229 A1 | | 9/2013 |
| DE | 10 2013 102 293 A1 | | 9/2014 |
| DE | 10 2014 108 066 A1 | | 12/2015 |
| DE | 102014114901 A1 | | 4/2016 |
| DE | 10306940 A1 | | 6/2019 |
| EP | 0682243 A1 | | 11/1995 |
| EP | 2500725 A1 | | 9/2012 |
| EP | 2713107 A1 | | 4/2014 |
| GB | 2098725 A | | 1/1982 |
| JP | S61265429 A | | 11/1986 |
| JP | H03144325 A | | 6/1991 |
| JP | H05209825 A | | 8/1993 |
| JP | 07127862 A | | 5/1995 |
| JP | H07127862 A | * | 5/1995 |
| JP | 2016014546 A | * | 7/2014 |
| JP | 2016014546 A | | 1/2016 |
| KR | 19930006905 B1 | | 7/1993 |
| KR | 1020150008936 A | | 1/2015 |
| KR | 1020170071159 A | | 6/2017 |
| KR | 101754372 B1 | | 7/2017 |
| WO | 2014/053002 A2 | | 4/2014 |
| WO | 2015/185211 A2 | | 12/2015 |
| WO | 2017/044161 A1 | | 3/2017 |
| WO | 2018188913 A1 | | 10/2018 |

OTHER PUBLICATIONS

Communication dated May 31, 2021, issued by the China National Intellectual Property Administration in Chinese Application No. 201880062929.3.
Communication dated May 26, 2020 issued by the European Patent Office in European Patent Application No. 18862835.8.
International Search Report (PCT/ISA/210) dated Oct. 26, 2018 from the International Searching Authority in counterpart application No. PCT/KR2018/007839.
Written Opinion (PCT/ISA/237) dated Oct. 26, 2018 from the International Searching Authority in counterpart application No. PCT/KR2018/007839.
Communication dated Aug. 25, 2021, issued by the Korean Intellectual Property Office in Korean Patent Application No. 10-2017-0128302.
Communication dated Dec. 30, 2021 issued by the China National Intellectual Property Administration in Chinese Application No. 201880062929.3.
Communication dated Jan. 12, 2022 issued by the European Patent Office in European Application No. 18862835.8.
Communication dated May 5, 2022 by the State Intellectual Property Office of P.R. China in counterpart English Chinese Patent Application No. 201880062929.3.
Communication dated Jan. 31, 2023 by the European Patent Office in European Application No. 18862835.8.

* cited by examiner

AUTOMATIC COOKING DEVICE AND METHOD

TECHNICAL FIELD

Provided are an automatic cooking device and method.

BACKGROUND ART

Artificial intelligence (AI) systems are computer systems capable of achieving human-level intelligence, and capable of training themselves, deciding, and becoming smarter, unlike existing rule-based smart systems. As use of such AI systems increases, recognition rates thereof further improve and users' preferences can be more accurately understood. Accordingly, the existing rule-based smart systems are gradually being replaced with deep-learning-based AI systems.

AI technology consists of machine learning (e.g., deep learning) and element technologies using machine learning.

Machine learning is an algorithm technology capable of classifying/learning features of input data autonomously. The element technologies are technologies for simulating functions of the human brain such as recognition, determination, etc. by using a machine learning algorithm such as deep learning, and consist of technical fields, including linguistic comprehension, visual comprehension, inference/prediction, knowledge representation, motion control, etc.

Various fields to which AI technology is applicable will be described below. Linguistic comprehension is technology for identifying and applying/processing human language/characters, and includes natural-language processing, machine translation, a dialogue system, query and response, speech recognition/synthesis, etc. Visual comprehension is technology for identifying and processing objects in terms of human perspective, and includes object recognition, object tracking, image searching, identification of human beings, scene comprehension, space comprehension, image enhancement, etc. Inference prediction is technology for identifying and logically reasoning information and making predictions, and includes knowledge/probability-based reasoning, optimization prediction, preference-based planning, recommendation, etc. Knowledge representation is technology for automatically processing human experience information according to knowledge data, and includes knowledge building (data generation/classification), knowledge management (data utilization), etc. Motion control is a technique for controlling self-driving of a vehicle and a robot's movement, and includes motion control (navigation, collision avoidance, traveling, etc.), operation control (behavior control), etc.

In the case of an oven for cooking food, a user directly inputs a kind of dish, a cooking method, setting information for cooking, and so on. However, the oven is complicated to set according to various recipes and even the same food material may have different characteristics such as different areas and thicknesses, and thus, there are cases in which it is not appropriate to use the oven according to a standard recipe. Accordingly, much attention has been paid to technology for applying artificial intelligence technology to cooking devices such as an oven to minimize the number of times the oven is manipulated by a user and to complete cooking in consideration of characteristics of a food material.

DESCRIPTION OF EMBODIMENTS

Technical Problem

Provided are an automatic cooking device and method for selectively emitting light of different wavelength bands to a food material, identifying the food material by obtaining information regarding the food material, based on reflected light, and controlling a cooking process of the food material.

Solution to Problem

The present disclosure relates to an artificial intelligence (AI) system for simulating functions, such as recognition and determination, of the human brain by using a machine learning algorithm such as deep learning, and an application thereof. Provided are an automatic cooking device and method for selectively emitting light of different wavelength bands to a food material, identifying the food material by obtaining information regarding the food material, based on reflected light, and controlling a cooking process of the food material.

BEST MODE

Figure 1:
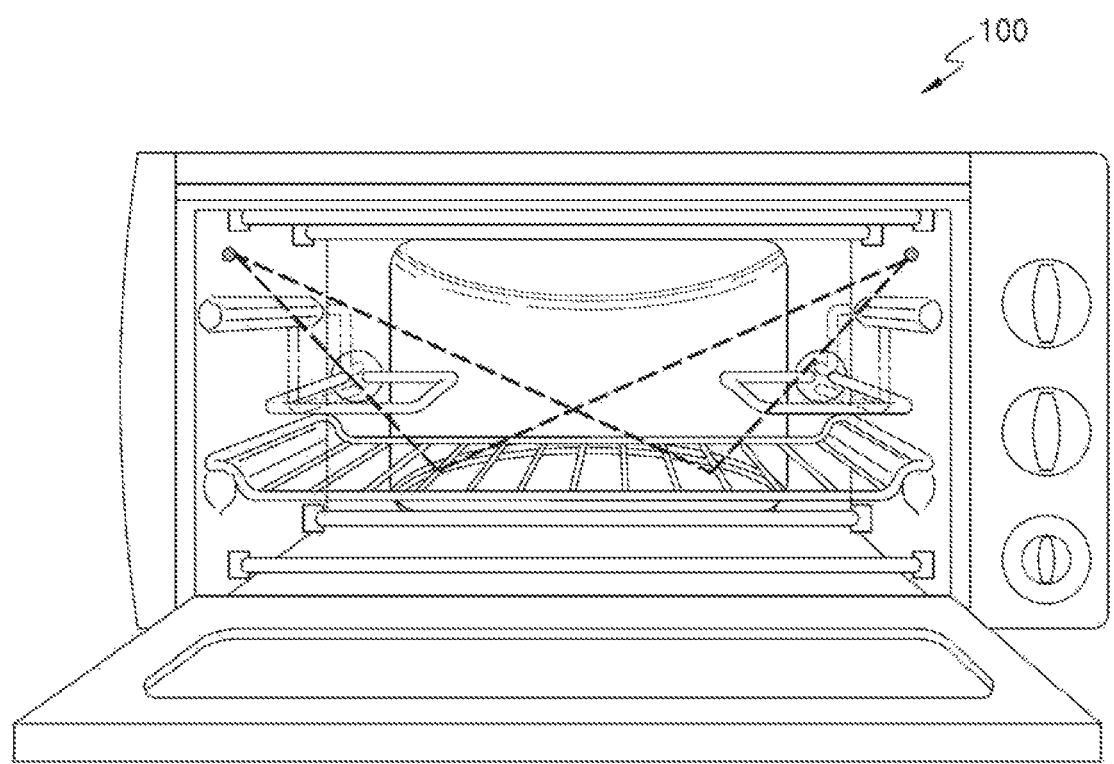
FIG. 1 is a diagram illustrating an automatic cooking device according to one embodiment.

According to a first aspect, an automatic cooking device includes a light emitter configured to emit light of different wavelength bands; a photographing unit including an image sensor; a memory storing computer executable instructions; at least one processor configured to execute the computer executable instructions to control the light emitter and the photographing unit to obtain information about a kind of a food material by performing vision recognition based on a captured image of the food material, obtain characteristic information of the food material by performing spectroscopic analysis based on light reflected by emitting light of a wavelength band selected according to the information about the kind of the food material, and control a cooking process of the food material, based on the information about the kind of the food material and the characteristic information of the food material; and a cooker configured to operate according to the cooking process of the food material.

According to a second aspect, an automatic cooking method includes obtaining information about a kind of a food material by performing vision recognition based on a captured image of the food material; obtaining characteristic information of the food material by performing spectroscopic analysis based on light reflected by emitting, to the food material, light of a wavelength band selected according to the information about the kind of the food material; and controlling a cooking process of the food material, based on the information about the kind of the food material and the characteristic information of the food material, wherein the information about the kind of the food material and the characteristic information of the food material are obtained by a light emitter which emits light of different wavelength bands and a photographing unit including an image sensor.

According to a third aspect, there is provided a non-transitory computer-readable recording medium storing a program for executing the automatic cooking method in a computer.

MODE OF DISCLOSURE

Hereinafter, embodiments to be provided as examples only will be described in detail with reference to the accompanying drawings. These embodiments are only intended to embody a technical concept but are not intended to restrict or limit the scope of the present disclosure. Matters easily derivable from the detailed description and embodiments by those of ordinary skill in the art should be construed as falling within the scope of the present disclosure.

In the present specification, it will be understood that when an element is referred to as being "connected" to another element, the element is 'directly connected' to the other element or is 'connected' to the other element with another element therebetween. It will be further understood that when an element is referred to as "including" another element, the element may further include other elements unless mentioned otherwise.

As used herein, the terms 'first', 'second,' etc. may be used to describe various components but the components should not be limited by the terms. These terms are used only for the purpose of distinguishing one component from another component.

As used herein, the term "automatic cooking device" collectively refers to an electronic device having a cooking function. For example, an oven, a microwave oven, or the like, which is food and beverage equipment that performs cooking by applying heat to a food material, may correspond to an automatic cooking device.

Embodiments set forth herein relate to an automatic cooking device and method, and matters well known to those of ordinary skill in the art to which these embodiments pertain will not be described in detail herein.

FIG. 1 is a diagram illustrating an automatic cooking device 100 according to one embodiment.

Referring to FIG. 1, an oven is illustrated as an example of the automatic cooking device 100 according to an embodiment. An operating method of the automatic cooking device 100 may be a convection method, a broil method, a high-temperature steam method, a grill method, or the like, but is not limited thereto and may be a combination of various methods. As illustrated in FIG. 1, various types of heating devices may be installed on upper, lower, and side portions of an internal space of the automatic cooking device 100, and some of the heating devices may be omitted and other heating devices may be added.

Referring to FIG. 1, a door of the automatic cooking device 100 is open so that a food material may be put into the internal space of the automatic cooking device 100, and a support is positioned at a height of a lower shelf of the automatic cooking device 100 so that the food material may be placed in the internal space. Referring to FIG. 1, the support on which a food material is to be placed is located at a height of one of two shelves, i.e., an upper shelf and the lower shelf, but is not limited thereto and may be provided at various types of shelves such as three, four, five, six or seven shelves so that food material may be cooked at any of various heights according to the kind, size, etc. of the food material. An operation part may be provided on an outer side of the automatic cooking device 100, through which a user input is input so that a user may control an operation of the automatic cooking device 100. The automatic cooking device 100 of FIG. 1 is provided with a dial type operation part, and a user may control the automatic cooking device 100 by rotating the dial type operation part by holding a handle thereof. However, the operating method of the automatic cooking device 100 is not limited to a dial method illustrated in FIG. 1, and may be any of various other methods such as a touch screen method and a button method providing a user interface.

Figure 2:
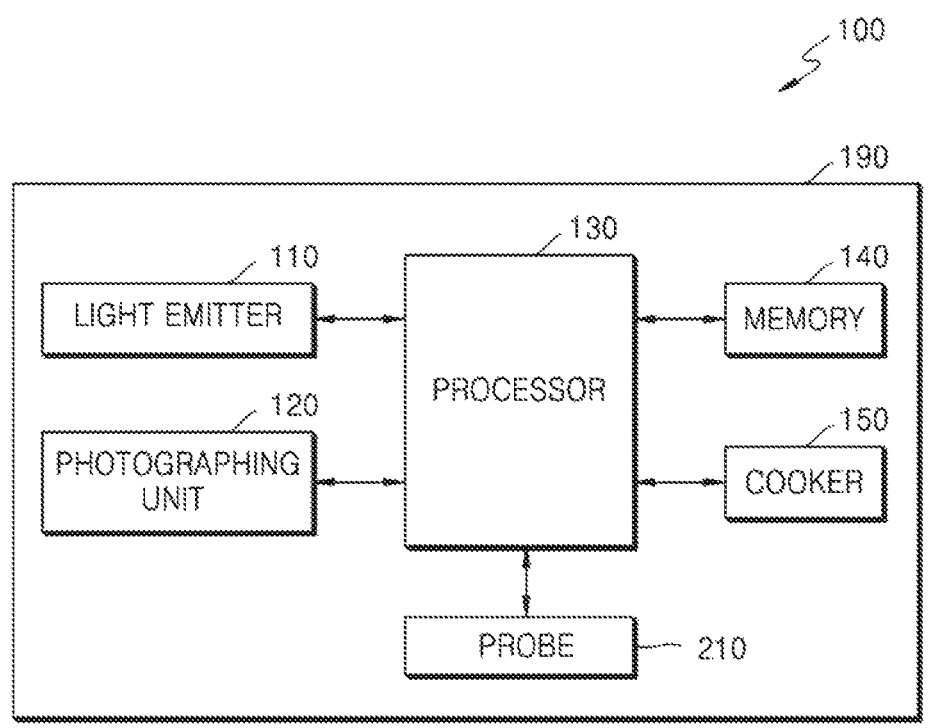
FIG. 2 is a block diagram for explaining an automatic cooking device according to an embodiment.

FIG. 2 is a block diagram for explaining an automatic cooking device 100 according to an embodiment.

It will be obvious to those of ordinary skill in the art that other general-purpose components may be further included, in addition to components illustrated in FIG. 2.

The automatic cooking device 100 may include a light emitter 110, a photographing unit 120, a processor 130, a memory 140, and a cooker 150.

The light emitter 110 may emit light of different wavelength bands. The light emitter 110 may sequentially emit light of different wavelength bands. For example, when a food material placed in an internal space of the automatic cooking device 100 is photographed, an image of the food material may be captured by sequentially emitting light of wavelength bands corresponding to red (R) color, green (G) color, and blue (B) color. In the automatic cooking device 100, light of a visible light region may be mainly used to photograph the food material in the internal space of the automatic cooking device 100, and a mixture of the light of the visible light region and light of an infrared region may be used when necessary. As another example, the automatic cooking device 100 may sequentially emit light of wavelength bands selected according to a kind of the food material. Because there is light of wavelength bands appropriate for identifying characteristics of the food material according to the kind of the food material, the automatic cooking device 100 may sequentially emit light of wavelength bands selected according to the kind of the food material in the internal space of the automatic cooking device 100 when information about the kind of the food material in the internal space of the automatic cooking device 100 is checked. The automatic cooking device 100 may select and use light of a certain wavelength band in a near-infrared region to identify the characteristics of the food material in the internal space of the automatic cooking device 100, and may use light of a visible light region when necessary.

As one example, the light emitter 110 may include a plurality of light-emitting elements each emitting light of a single wavelength band, and a light guide which provides a path through which light emitted from a light-emitting element selected from among the plurality of light-emitting elements travels.

As another example, the light emitter 110 may include a light-emitting element which emits light of multiple wavelength bands, a band pass filter which allows light of a wavelength band selected from among the multiple wavelength bands to pass therethrough, and a light guide providing a path through which the light of the selected wavelength band travels.

The photographing unit 120 is a component that generates an image of an electrical signal from light incident thereon and may include at least one image sensor. In this case, the image sensor may be a charge coupled device (CCD) which converts an optical signal into an electrical signal or a complementary metal oxide semiconductor (CMOS) image sensor. The photographing unit 120 may capture an image by using light of a single wavelength band emitted from the light emitter 110. The photographing unit 120 may capture an image by using light of a single wavelength band and thus may not use a filter to pass light of a single wavelength band. However, in some cases, the photographing unit 120 may include a band pass filter to pass light of certain single wavelength bands.

The photographing unit 120 may further include a noise reduction filter that adjusts light of a noise wavelength band which is incident on the image sensor. The photographing unit 120 may further include a lens and a lens driving unit for adjusting a position of the lens.

The memory 140 may store a program for processing and control performed by the processor 130 and store data input to or output from the automatic cooking device 100. The memory 140 may store computer executable instructions.

Generally, the processor 130 controls overall operations of the automatic cooking device 100. The processor 130 may include at least one processor. The processor 130 may include a plurality of processors or an integrated processor according to a function and role thereof.

The processor 130 may execute the computer executable instructions stored in the memory 140 to control the light emitter 110 and the photographing unit 120 to obtain information about the kind of a food material by vision recognition based on a captured image of the food material and obtain characteristic information of the food material by an spectroscopic analysis based on light reflected by emitting light of wavelengths selected according to the information about the kind of the food material. The characteristic information of the food material may include a composition ratio of the food material, an acidity level (PH), water content, and the like.

The processor 130 may further perform the spectroscopic analysis on the food material according to the information about the kind of the food material obtained by vision recognition to obtain detailed information of the food material. The processor 130 may further perform the spectroscopic analysis on the kind of a certain food material to obtain more accurate information about the kind of the food material or additional information of the food material.

The processor 130 may select a wavelength band corresponding to the information about the kind of the food material, determine the amount of light of the selected wavelength band according to the position of the food material and the intensity of external light, emit the light of the selected wavelength band to the food material, perform calibration according to the position of the food material and the intensity of the external light during the spectroscopic analysis based on the reflected light, and obtain the characteristic information of the food material. The processor 130 may select a wavelength band appropriate for detection of characteristic information, such as the amount of protein, fat content, water content, and an acidity level, of each food material, based on a database of food material information. The processor 130 may remove noise caused by external light with respect to the selected wavelength band and perform the spectroscopic analysis.

The processor 130 may control a cooking process of the food material, based on the information about the kind of the food material and the characteristic information of the food material. The processor 130 may obtain an optimum recipe using the food material and control the cooking process according to the recipe by comparing the information about the kind of the food material and the characteristic information of the food material before cooking with the database of food material information. The processor 130 may control the cooking process of the food material by identifying a cooked state of the food material, based on the characteristic information of the food material, and determining at least one of a cooking method, a cooking time, or a cooking temperature, based on the cooked state to the food material. The cooking method may be a grilling method, a convection method, a steam method, a radio-frequency (RF) cooking method, or the like. The cooking time may refer to a time period set for completion of cooking of the food material, a time elapsed from a cooking start time, or the like. The cooking temperature may refer to a temperature set for the completion of cooking of the food material, a current temperature in the cooking process, or the like.

The processor 130 may identify a current cooking stage when a certain time elapses or when there is a change in the cooked state of the food material during the control of the cooking process, based on the characteristic information of the food material in the cooking process, and may set, change or maintain the cooking method, the cooking time, the cooking temperature, etc., based on an actual cooked state.

The processor 130 may estimate the cooked state or the end of cooking time of the food material by selectively emitting light of a wavelength band used for obtaining predefined sensing information according to the progress of the cooking process of the food material. For example, the processor 130 may obtain denaturation information of a surface of the food material, in particular, protein denaturation information by the spectroscopic analysis, and control the cooking process according to a schedule for optimizing a cooking temperature or time, based on protein modification.

The processor 130 may define sensing information to be detected in advance according to the progress of the cooking process of the food material, and identify a degree of doneness of the food material by the spectroscopic analysis based on light reflected by selectively emitting light of a wavelength band used for obtaining such sensing information. For example, when a cooking process of a steak is performed sequentially by surface drying, surface scorching, and complete baking, the processor 130 may set sensing information required to detect surface water content of the steak in the surface drying, detect protein denaturation information in the surface scorching, and detect not only protein denaturation information but also information of a change in the thickness or volume of the food material in the complete baking, and set wavelength bands for obtaining the sensing information in advance.

When the automatic cooking device 100 is capable of measuring the volume of a food material, the processor 130 may control the cooking process of the food material by identifying a cooked state of the food material, based on the characteristic information of the food material and volume change information regarding the difference between volume of the food material before cooking and volume of the food material when heated. To this end, the automatic cooking device 100 may measure the volume of the food material by applying an algorithm for volume estimation to a captured image or may further include a volume measuring device for measuring the volume of a food material.

When the automatic cooking device 100 further includes a probe 210 to obtaining information about an internal temperature and composition of the food material, the processor 130 may control the cooking process of the food material by identifying a cooked state of the food material, based on the characteristic information of the food material and the information about the internal temperature and composition of the food material. In this case, the processor 130 may identify a position of the probe 210 by the photographing unit 120 and inform a user of the position of the probe 210 to correct the position of the probe.

The processor 130 may be trained with a criterion for identifying which region of an image of the food material, which is captured using at least one piece of light of a single wavelength band of a visible light region and/or a near infrared region, corresponds to a food material region or a region representing characteristic information so as to estimate the kind of or characteristic information of the food material. The processor 130 may be trained with a criterion for determining which data is to be used to identify which region of the image corresponds to a food material region or a region representing characteristic information and a criterion for determining how to identify which region of the image corresponds to a food material region or a region representing characteristic information by using the data. The processor 130 may be trained with a criterion for identifying which region of the image corresponds to a food material region or a region representing characteristic information by obtaining data to be used for training and applying the obtained data to a data recognition model to be described later.

The processor 130 may identify which region of the image corresponds to a food material region or a region representing characteristic information, based on information about various kinds of food materials.

The processor 130 may be manufactured in the form of a dedicated hardware chip for artificial intelligence (AI) or manufactured using an existing general-purpose processor (e.g., a CPU or an application processor), a graphics-dedicated processor (e.g., a GPU), or the like, and mounted in the automatic cooking device 100.

The processor 130 may obtain data necessary for learning a criterion for identifying which region of the image corresponds to a food material region or a region representing characteristic information. For example, the processor 130 may obtain image data, for example, an image, a video, or the like. The processor 130 may obtain data directly input to or selected by the automatic cooking device 100, set data, or the like.

The processor 130 may obtain data input from a user, data captured by or stored in the automatic cooking device 100 in advance, data received from an external device, or the like but embodiments are not limited thereto.

The processor 130 may remove noise from data such as an image or video or process the data in a certain form to select meaningful data.

The processor 130 may be provided with a data selection criterion for each type of data such as an image or a video and may select data necessary for learning by using this criterion. The processor 130 may obtain data necessary to be trained to learn which region of an image corresponds to a food material region or a region representing characteristic information.

The processor 130 may be trained with a criterion for identifying which region of the image corresponds to a food material region or a region representing characteristic information, based on training data. In addition, the processor 130 may be trained with a criterion for determining which training data should be used to identify which region of the image corresponds to a food material region or a region representing characteristic information.

The processor 130 may be trained as to how to identify which region of the image corresponds to a food material region or a region representing characteristic information. For example, the processor 130 may be trained as to how to identify which region of the image corresponds to a food material region by a first data recognition model. In addition, the processor 130 may be trained as to how to identify which region of the image corresponds to region representing characteristic information by a second data recognition model.

In addition, the processor 130 may train a data recognition model, which is used to identify which region of the image corresponds to a food material region or a region representing characteristic information, using the training data.

The data recognition model may be a model based on a neural network. For example, a model such as a deep neural network (DNN) may be used as the data recognition model but embodiments are not limited thereto.

The processor 130 may train the data recognition model by supervised learning, unsupervised learning, reinforcement learning using feedback, or the like.

The processor 130 may input evaluation data to the data recognition model, and retrain the data recognition model when a recognition result output according to the evaluation data does not satisfy a certain criterion.

The processor 130 may identify which region of an image corresponds to a food material region or a region representing characteristic information by using the trained data recognition model.

The processor 130 may obtain various types of data to identify which region of the image corresponds to a food material region or a region representing characteristic information. For example, the processor 130 may obtain image data such as an image, a video, or the like. For example, the processor 130 may obtain data directly input to or selected by the automatic cooking device 100, or the like or obtain information sensed by various types of sensors of the automatic cooking device 100.

The processor 130 may preprocess obtained data or information to use the obtained data or information to identify which region of the image corresponds to a food material region or a region representing characteristic information. For example, the processor 130 may remove noise from image data such as an image or a video or process the image data in a certain form to select meaningful data.

The processor 130 may select data necessary to identify which region of the image corresponds to a food material region or a region representing characteristic information.

The processor 130 may apply the selected data to the data recognition model so as to identify which region of the image corresponds to a food material region or a region representing characteristic information.

The processor 130 may identify which region of the image of the food material captured by using at least one piece of light of a single wavelength band of a visible light region and/or a near infrared region corresponds to a food material region or a region representing characteristic information, and estimate the kind of or characteristic information of the food material.

The processor 130 may re-estimate a current state or cooked state of the food material by comparing the estimated kind or characteristic information of the food material with a database of food material information, and control the cooking process, based on the re-estimated state or cooked state of the food material.

The cooker 150 may operate according to a cooking process of a food material controlled by the processor 130. The cooker 150 may be a heating device for baking a food material, a steamer used in the cooking process of the food material, or the like. The cooker 150 may be various types of heating means according to a cooking method. The cooker 150 may further include partial heating means or additional heating means, together with heating means mainly used in the automatic cooking device 100.

Figure 3:
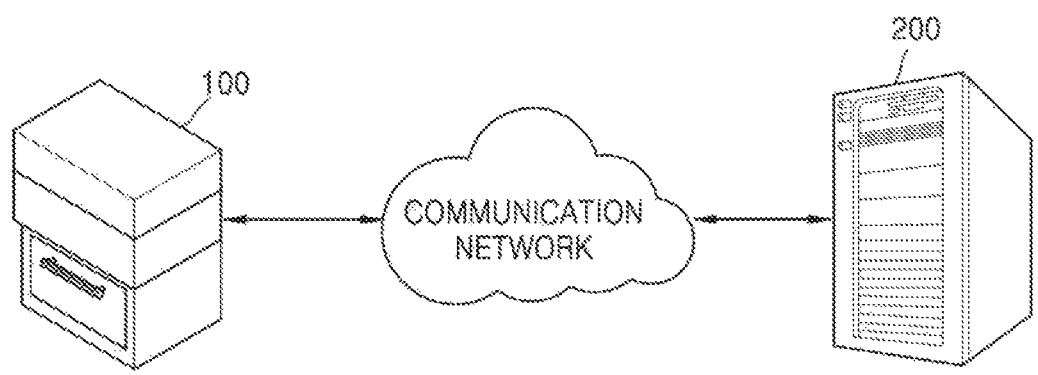
FIG. 3 is a diagram illustrating a process of training an automatic cooking device to learn and identify information regarding a food material in connection with a server, according to an embodiment.

FIG. 3 is a diagram illustrating a process of training an automatic cooking device 100 to learn and identify information regarding a food material, in connection with a server 200, according to an embodiment.

Referring to FIG. 3, the server 200 may collect various types of information related to a food material and store a database of food material information. The server 200 may check various image data of the food material and be trained with a criterion for identifying which region of the image corresponds to a food material region or a region representing characteristic information. The automatic cooking device 100 may identify which region of the image corresponds to a food material region or a region representing characteristic information by using a data recognition model trained by the server 200.

The server 200 may be trained with a criterion for identifying which data is to be used to identify which region of the image corresponds to a food material region or a region representing characteristic information, and a criterion for determining how to identify which region of the image corresponds to a food material region or a region representing characteristic information by using the data. The processor 130 may be trained with a criterion for identifying which region of the image corresponds to a food material region or a region representing characteristic information by obtaining data to be used for training and applying the obtained data to the data recognition model.

The automatic cooking device 100 may receive the data recognition model trained by the server 200 and identify which region of the image corresponds to a food material region or a region representing characteristic information. Alternatively, the automatic cooking device 100 may transmit a captured image of the food material to the server 200, request the server 200 to apply the image to the data recognition model and identify which region of the image corresponds to a food material region or a region representing characteristic information, and receive a result of the identification from the server 200.

The automatic cooking device 100 may identify which region of an image of the food material captured by using at least one piece of light of a single wavelength band of a visible light region and/or a near infrared region corresponds to a food material region or a region representing characteristic information, and estimate the kind or characteristic information of the food material. The processor 130 may re-estimate a current state or cooked state of the food material by comparing the estimated kind or characteristic information of the food material with a database of food material information, and control the cooking process, based on the re-estimated state or cooked state of the food material.

Figure 4:
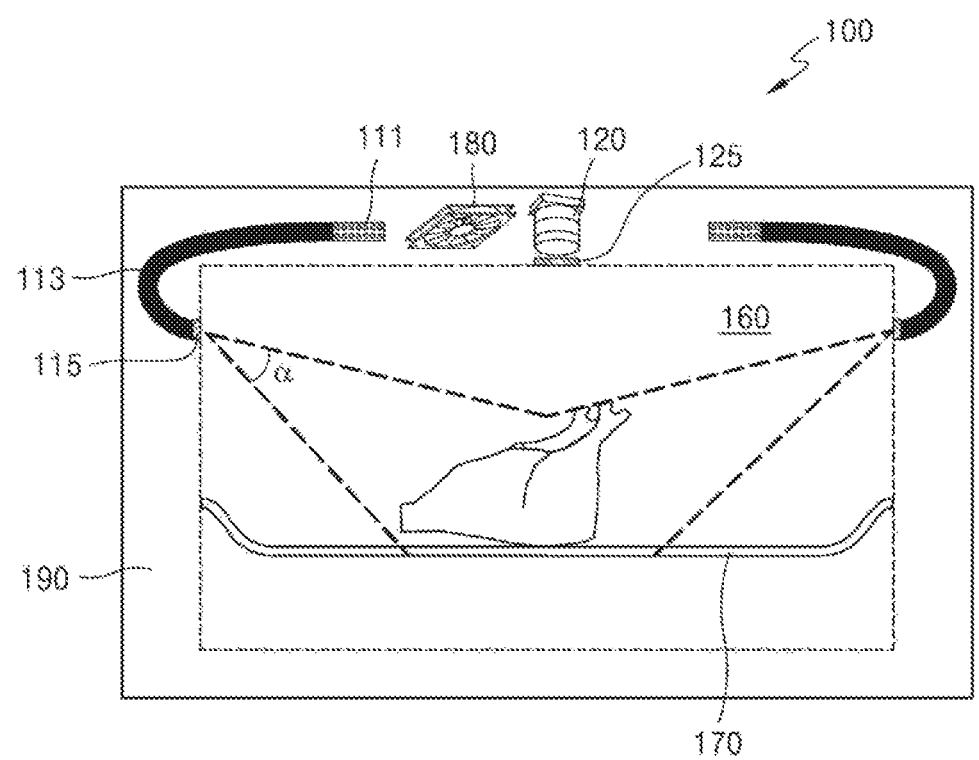
FIG. 4 is a diagram for explaining a structure and operation of an automatic cooking device according to an embodiment.

FIG. 4 is a diagram for explaining a structure and operation of an automatic cooking device 100 according to an embodiment.

Referring to FIG. 4, a support 170 on which a food material is to be placed is installed in an internal space 160 of the automatic cooking device 100, and the food material is placed on the support 170. In the automatic cooking device 100, the food material may be placed on the support 170 in the internal space 160 and the internal space 160 may be air-tightly closed to cook the food material by opening and closing a door. A location at which the support 170 is installed may vary according to the kind of the food material. In the automatic cooking device 100, a height of the support 170 may be adjusted according to information about the kind of the food material.

Referring to FIG. 4, in the automatic cooking device 100, light is emitted to the food material on the support 170 in the internal space 160. To this end, the automatic cooking device 100 may include a light emitter 110 and the light emitter 110 may be implemented in various ways, in consideration of the use, performance, and the like of the automatic cooking device 100.

As illustrated in FIG. 4, the light emitter 110 may include a plurality of light-emitting elements 111 each of which emits light of a single wavelength band, and a light guide 113 providing a path through which light emitted from a light-emitting element 111 selected from the plurality of light-emitting elements 111 travels. The plurality of light-emitting elements 111 may be in the form of a light-emitting element array, and each of the plurality of light-emitting elements 111 may be a light-emitting diode (LED) emitting light of a single wavelength band. Unlike that illustrated in FIG. 4, the light emitter 110 may include a light-emitting element (not shown) which emits light of multiple wavelength bands, a band pass filter (not shown) which allows light of a wavelength band selected from among the multiple wavelength bands to pass therethrough, and the light guide 113 providing a path through which light of the selected wavelength band travels.

Referring to FIG. 4, the light emitter 110 is installed such that light emitted from the plurality of light-emitting elements 111 which are in an array form may be emitted to the food material in the internal space 160 of the automatic cooking device 100 via the light guide 113. The plurality of light-emitting elements 111 which are in the array form may be mounted in a housing 190 forming the inner space 160 of the automatic cooking device 100. The housing 190 may be a frame in which the components of the automatic cooking device 100 may be mounted and may serve as a muffle which blocks heat generated from the automatic cooking device 100 from being discharged to the outside. The light guide 113 is a medium, such as a fiber optic cable, via which light is transmitted, and may provide a path through which light emitted from the plurality of light-emitting elements 111 travels. One end of the light guide 113 may be in contact with the plurality of light-emitting elements 111 which emit light. Other ends of the light guide 113 may be located on left and right side portions of the inner space 160 of the automatic cooking device 100 as illustrated in FIG. 4 so that light passing through the light guide 113 may be emitted to the food material, but embodiments are not limited thereto. In order to minimize light saturation, the light emitter 110 may emit light to the food material at an incident angle of about 45 degrees but the incident angle with respect to the food material is not limited thereto. As illustrated in FIG. 4, the light guide 113 is disposed in the housing 190 of the automatic cooking device 100 and a first heat resistant window 115 is disposed an end of the light guide which emits light. The light emitter 110 may emit light to the food material at an angle α.

In the housing 190 of the automatic cooking device 100, a photographing unit 120 may be mounted and a second heat resistant window 125 may be positioned at a front end of the photographing unit 120 on which light is incident.

A cooling fan 180 may cool the light emitter 110 and the photographing unit 120 and be disposed at an appropriate location on the housing 190 in consideration of the size, function, operation method, and the like of the automatic cooking device 100. For example, the cooling fan 180 may be disposed at a location suitable for cooling both the light-emitting elements 111 of the light emitter 110 and the photographing unit 120, and a plurality of cooling fans 10 may be disposed according to positions of the light-emitting elements 111 and the photographing unit 120.

Figure 5:
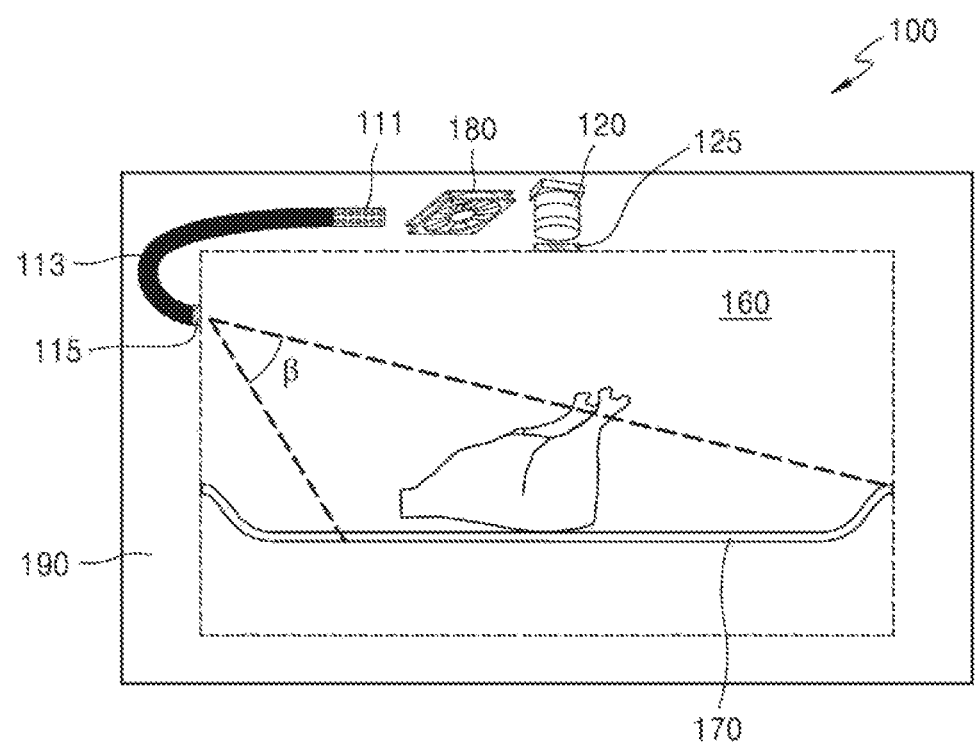
FIG. 5 is a diagram for explaining a structure and operation of an automatic cooking device according to another embodiment.

FIG. 5 is a diagram for explaining a structure and operation of an automatic cooking device 100 according to another embodiment.

A description of parts of FIG. 5 which are the same as those described above with reference to FIG. 4 will be omitted herein.

Referring to FIG. 5, light is emitted to a food material on a support 170 in an internal space 160 of the automatic cooking device 100 as illustrated in FIG. 4 but one light emitter 110 is provided unlike in FIG. 4. As illustrated in FIG. 5, the light emitter 110 may be located on one of side portions of the internal space 160 of the automatic cooking device 100 but embodiments are not limited thereto. In order to emit light at a higher position, the light emitter 110 may be located at the top of a side portion of or an edge of an upper portion of the inner space 160 of the automatic cooking device 100.

The light emitter 110 may emit light to a food material at an angle β. In FIG. 4, the light emitters 110 are located at both sides of the internal space 160 of the automatic cooking device 100, whereas in FIG. 5, the light emitter 110 is located at a side of the internal space 160 of the automatic cooking device 100 and may emit light to the food material at an emission angle β which is greater than or equal to the emission angle α of FIG. 4.

Figure 6:
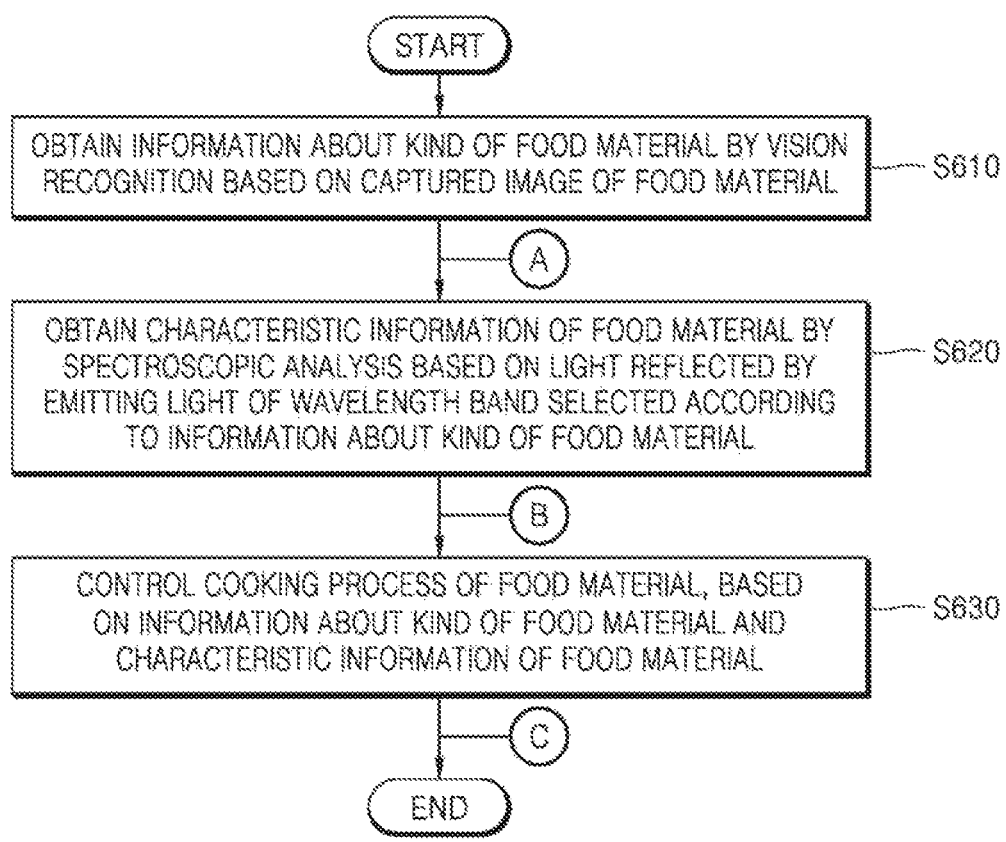
FIG. 6 is a flowchart of an automatic cooking method according to one embodiment.

FIG. 6 is a flowchart of an automatic cooking method according to an embodiment.

In operation 610, the automatic cooking device 100 may obtain information about the kind of a food material by vision recognition based on a captured image of the food material. The information about the kind of the food material may be obtained by controlling a light emitter, which emits light of different wavelength bands, and a photographing unit with an image sensor. The automatic cooking device 100 may further perform the spectroscopic analysis with respect to the food material according to the information about the kind of the food material, which is obtained by vision recognition, to obtain detailed information of the food material. The automatic cooking device 100 may further perform the spectroscopic analysis with respect to the kinds of certain food materials to obtain more accurate information or additional information about the kinds of the food materials.

In operation 620, the automatic cooking device 100 may obtain characteristic information of the food material by the spectroscopic analysis based on light reflected by emitting light of a wavelength band selected according to information about the kind of the food material. The characteristic information of the food material may be obtained by controlling a light emitter, which emits light of different wavelength bands, and a photographing part with an image sensor.

Figure 7:
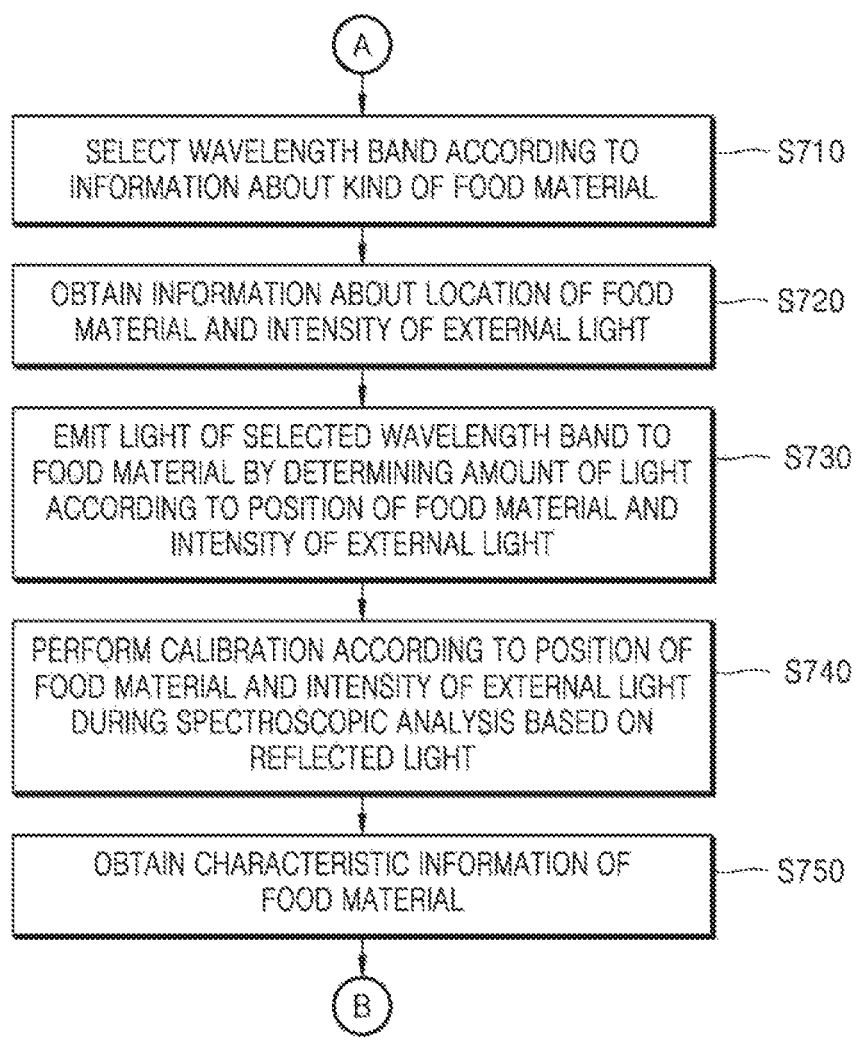
FIG. 7 is a detailed flowchart of a process of obtaining characteristic information of a food material by spectroscopic analysis, the process being included in an automatic cooking method, according to an embodiment.

FIG. 7 is a detailed flowchart of a process of obtaining characteristic information of a food material by spectroscopic analysis, the process being included in an automatic cooking method, according to an embodiment.

In operation 710, the automatic cooking device 100 may select a wavelength band according to information about the kind of a food material.

In operation 720, the automatic cooking device 100 may obtain information about the location of the food material and the intensity of external light. For example, the automatic cooking device 100 may analyze a captured image of the food material or identify the location of the food material by sensing a height of a support on which the food material is placed. In the automatic cooking device 100, when a spectral image of a single wavelength band is captured for each of the light-emitting elements 111 that each emit light of a single wavelength band, the intensity of external light in a certain wavelength band may be identified by identifying a saturation time according to control of the intensity of light from a certain light-emitting element 111. The automatic cooking device 100 may measure the intensity of the external light by using a separate external-light sensor which measures the intensity of external light.

In operation 730, the automatic cooking device 100 may emit light of a selected wavelength band to the food material by identifying the amount of light according to the position of the food material and the intensity of the external light.

In operation 740, the automatic cooking device 100 may perform calibration according to the position of the food material and the intensity of the external light during the spectroscopic analysis based on reflected light. For example, in the automatic cooking device 100, the intensity of light emitted from the light-emitting elements 111 may be changed according to the intensity of the external light, and a calibration weight may be determined according to the intensity of the light emitted from the light-emitting elements 111. The automatic cooking device 100 may perform calibration by removing a value corresponding to the intensity of the external light from the captured image and multiplying a result of removing the value by the calibration weight.

In operation 750, the automatic cooking device 100 may obtain characteristic information of the food material.

Referring back to FIG. 6, in operation 630, the automatic cooking device 100 may control a cooking process of the food material, based on the information about the kind of the food material and the characteristic information of the food material.

Figure 8:
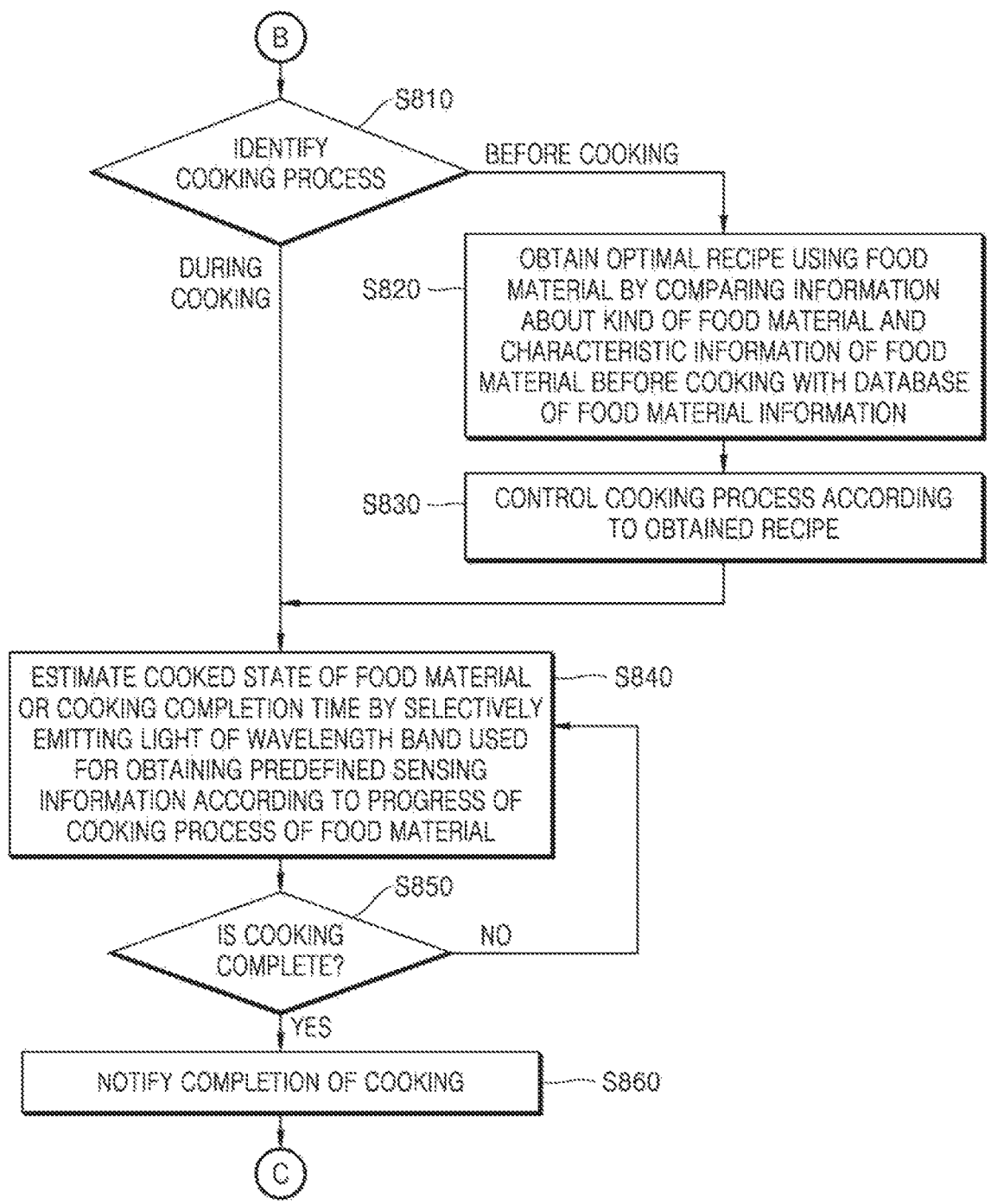
FIG. 8 is a detailed flowchart of a process of controlling a cooking process, the process being included in an automatic cooking method, according to an embodiment.

FIG. 8 is a detailed flowchart of a process of controlling a cooking process, the process being included in an automatic cooking method, according to an embodiment.

In operation 810, the automatic cooking device 100 may identify a cooking process by identifying a current state thereof. The automatic cooking device 100 may identify whether cooking is being performed therein or has yet to be performed, and perform settings for cooking when cooking has yet to be performed and perform the cooking process to complete cooking when cooking is being performed.

In operation 820, when it is determined that cooking has yet to be performed, the automatic cooking device 100 may obtain an optimal recipe using a food material by comparing information about the kind and characteristic information of the food material before cooking with a database of food material information.

In operation 830, the automatic cooking device 100 may control the cooking process according to the obtained recipe. For example, the automatic cooking device 100 may determine a cooking method, a cooking time, a cooking temperature, etc. according to information regarding the recipe, which is included in the database of food material information, and operate according to the determined cooking method, cooking time, the cooking temperature, etc. Without user input, the automatic cooking device 100 may identify the food material, identify a current state of the food material, and start cooking to perform the cooking process of the food material according to a recipe most suitable for the current state of the food material.

In operation 840, when it is determined that cooking is being performed, the automatic cooking device 100 may estimate a cooked state of the food material or a cooking completion time by selectively emitting light of a wavelength band used for obtaining predefined sensing information according to the progress of the cooking process of the food material. The automatic cooking device 100 may control the cooking process of the food material by identifying the cooked state of the food material, based on the characteristic information of the food material, and determining at least one of a cooking method, a cooking time, or a cooking temperature, based on the cooked state to the food material. The automatic cooking device 100 may operate a heating mechanism for heating a certain portion or part when there is a portion or part to be partially or additionally heated, based on a cooking state of each portion or part of the food material. For example, when a cooked level of a certain portion of the food material is lower than those of the other portions thereof, the certain portion of the food material may be partially heated by microwaves, light waves, high-frequency waves or the like. When the entire food material is to be cooked at a faster speed, the food material may be cooked using additional heating means together with a main heating means.

When it is determined based on a current cooked state of the food material that it is necessary to correct an initially set cooking method, time or temperature according to the optimal recipe, the automatic cooking device 100 may add a new set value or change or maintain a set value of an item to be changed.

When the automatic cooking device 100 is capable of measuring the volume of the food material, the automatic cooking device 100 may control the cooking process of the food material by identifying a more accurate cooked state the food material, based on the characteristic information of the food material and volume change information regarding the difference between the volume of the food material before cooking and the volume of the food material when heated.

When the automatic cooking device 100 further obtains information about an internal temperature and composition of the food material by using a probe 210 for obtaining information about an internal temperature and composition of a food material, the automatic cooking device 100 may control the cooking process of the food material by identifying a more accurate cooked state of the food material, based on the characteristic information of the food material and the information about the internal temperature and composition of the food material. In this case, the automatic cooking device 100 may identify a position of the probe 210 by the photographing unit 120 and inform a user of the position of the probe 210 to correct the position of the probe 210. The automatic cooking device 100 may obtain the information about the internal temperature and composition of the food material at the changed position of the probe 210. The automatic cooking device 100 may identify and learn the current cooked state of the food material more accurately, based on the information about the internal temperature and composition of the food material, which is obtained by the probe 210, and the characteristic information of the food material obtained by the spectroscopic analysis, and control a current cooking process according to the current cooked state or reflect the current cooked state for future cooking process control.

In operation 850, the automatic cooking device 100 may identify whether cooking of the food material is completed. When the cooking of the food material is not completed, the automatic cooking device 100 may perform operation 840 again.

In operation 860, when the cooking of the food material is completed, the automatic cooking device 100 may notify the completion of the cooking. In this case, the automatic cooking device 100 may inform a user of information regarding a cooked dish and how to eat the dish.

The automatic cooking method described above may be embodied as a computer executable program and implemented in a general-purpose digital computer for execution of the program via a computer-readable storage medium. Examples of the computer-readable storage media include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tape, floppy disks, magneto-optical data storage devices, optical data storage devices, hard disks, solid-state disks (SSDs), and any other devices capable of storing instructions or software, relevant data, data files, and data structures and providing them to processors or computers to execute the instructions.

Various embodiments have been described above. It will be understood by those of ordinary skill in the art that the embodiments set forth herein may be embodied in many different forms without departing from essential features of the present disclosure. Therefore, the embodiments set forth herein should be considered in a descriptive sense only and not for purposes of limitation. The scope of the present disclosure is set forth in the claims rather than in the foregoing description of embodiments, and all differences falling within a scope equivalent thereto should be construed as being included in the scope of the present disclosure.

The invention claimed is:

1. An automatic cooking device comprising:
   a light emitter configured to emit light of different wavelength bands;
   a photographing unit including an image sensor;
   a memory storing computer executable instructions;
   at least one processor configured to execute the computer executable instructions to control the light emitter and the photographing unit to obtain information about a kind of a food material by performing vision recognition based on a captured image of the food material, obtain characteristic information of the food material by performing spectroscopic analysis based on light reflected by emitting light of a wavelength band selected from among the different wavelength bands according to the information about the kind of the food material, and control a cooking process of the food material, based on the information about the kind of the food material and the characteristic information of the food material; and a probe configured to obtain information about internal temperature and composition of the food material;

a cooker configured to operate according to the cooking process of the food material, wherein the at least one processor is further configured to identify a position of the probe by using the photographing unit, and to control the cooking process of the food material by identifying a cooked state of the food material, based on the characteristic information of the food material and the information about the internal temperature and composition of the food material, and wherein the position of the probe is changeable by a user.

2. The automatic cooking device of claim 1, wherein the at least one processor is further configured to:

select a wavelength band corresponding to the information about the kind of the food material;

identify an amount of light of the selected wavelength band according to a position of the food material and an intensity of external light and emit the light of the selected wavelength band to the food material;

perform calibration according to the position of the food material and the intensity of the external light during the spectroscopic analysis based on the reflected light; and obtain the characteristic information of the food material.

3. The automatic cooking device of claim 1, wherein the at least one processor is further configured to obtain an optimum recipe using the food material and control the cooking process according to the recipe by comparing the information about the kind of the food material and the characteristic information of the food material before cooking with a database of food material information.

4. The automatic cooking device of claim 1, wherein the at least one processor is further configured to estimate the cooked state of the food material or an end of a cooking time by selectively emitting light of a wavelength band used for obtaining predefined sensing information according to a progress of the cooking process of the food material.

5. The automatic cooking device of claim 1, wherein the at least one processor is further configured to control the cooking process of the food material by identifying the cooked state of the food material, based on the characteristic information of the food material and volume change information regarding a difference between a volume of the food material before cooking and the volume of the food material when heated.

6. An automatic cooking method comprising:

obtaining information about a kind of a food material by performing vision recognition based on a captured image of the food material;

obtaining characteristic information of the food material by performing spectroscopic analysis based on light reflected by emitting, to the food material, light of a wavelength band selected from among different wavelength bands according to the information about the kind of the food material;

obtaining information about internal temperature and composition of the food material by identifying a position of a probe configured to obtain the information about the internal temperature and composition of the food material; and controlling a cooking process of the food material, based on the information about the kind of the food material and the characteristic information of the food material, wherein the information about the kind of the food material and the characteristic information of the food material are obtained by a light emitter which emits light of the different wavelength bands and a photographing unit including an image sensor, wherein the controlling of the cooking process of the food material comprises controlling the cooking process of the food material by identifying a cooked state of the food material, based on the characteristic information of the food material and the information about the internal temperature and composition of the food material, and wherein the position of the probe is changeable by a user.

7. The automatic cooking method of claim 6, wherein the obtaining of the characteristic information of the food material by performing the spectroscopic analysis comprises:

selecting a wavelength band according to the information about the kind of the food material;

emitting light of the selected wavelength band to the food material by determining an amount of the light according to a position of the food material and an intensity of external light;

performing calibration according to the position of the food material and the intensity of the external light during the spectroscopic analysis based on the reflected light; and obtaining the characteristic information of the food material.

8. The automatic cooking method of claim 6, wherein the controlling of the cooking process of the food material comprises:

obtaining an optimal recipe using the food material by comparing the information about the kind of the food material and the characteristic information of the food material before cooking with a database of food material information; and controlling the cooking process according to the obtained recipe.

9. The automatic cooking method of claim 6, wherein the controlling of the cooking process of the food material comprises estimating athe cooked state of the food material or an end of a cooking time by selectively emitting light of a wavelength band used for obtaining predefined sensing information according to a progress of the cooking process of the food material.

10. The automatic cooking method of claim 6, further comprising obtaining volume change information regarding a difference between a volume of the food material before cooking and the volume of the food material when heated, and wherein the controlling of the cooking process of the food material comprises controlling the cooking process of the food material by identifying the cooked state of the food material, based on the characteristic information of the food material and the volume change information.

11. A non-transitory computer-readable recording medium storing a program for executing the method of claim 6 in a computer.

* * * * *